United States Patent
Casagranda et al.

(10) Patent No.: US 12,369,811 B2
(45) Date of Patent: Jul. 29, 2025

(54) METHOD FOR ATTENUATING THE NOISE IN IMAGES RESULTING FROM MULTIPLE ACQUISITIONS BY MAGNETIC RESONANCE IMAGING

(71) Applicant: OLEA MEDICAL, La Ciotat (FR)

(72) Inventors: Stefano Casagranda, Bussero (IT); Christos Papageorgakis, La Ciotat (FR); Mauro Zucchelli, Antibes (FR)

(73) Assignee: OLEA MEDICAL, La Ciotat (FR)

( * ) Notice: Subject to any disclaimer, the term of this patent is extended or adjusted under 35 U.S.C. 154(b) by 351 days.

(21) Appl. No.: 18/185,053

(22) Filed: Mar. 16, 2023

(65) Prior Publication Data

US 2023/0225630 A1 Jul. 20, 2023

Related U.S. Application Data

(63) Continuation-in-part of application No. PCT/FR2022/051278, filed on Jun. 28, 2022.

(30) Foreign Application Priority Data

Jun. 29, 2021 (FR) ........................ 2107003

(51) Int. Cl.
- *A61B 5/055* (2006.01)
- *A61B 5/00* (2006.01)
- *G06T 7/00* (2017.01)

(52) U.S. Cl.
CPC ............ *A61B 5/055* (2013.01); *G06T 7/0012* (2013.01); *A61B 5/0042* (2013.01)

(58) Field of Classification Search
None
See application file for complete search history.

(56) References Cited

U.S. PATENT DOCUMENTS

| 6,009,208 A | 12/1999 | Mitra et al. |
| 2019/0086496 A1 * | 3/2019 | Moeller ................ G06T 7/0012 |

FOREIGN PATENT DOCUMENTS

| FR | 2931935 A1 * | 12/2009 | ........... G06T 7/0081 |
| JP | H09-138853 A | 5/1997 | |

(Continued)

OTHER PUBLICATIONS

Veraart et al., "Denoising of diffusion MRI using random matrix theory", Neuroimage, Aug. 2016, vol. 142, pp. 394-406 (Year: 2016).*

(Continued)

*Primary Examiner* — Miya J Cato
(74) *Attorney, Agent, or Firm* — BUCHANAN, INGERSOLL & ROONEY PC

(57) ABSTRACT

A system and method for denoising experimental data originating from multiple acquisitions by a magnetic resonance imaging device, by analysis of selected principal components, to obtain a better compromise between the efficiency of the denoising and retention of the relevant information in the experimental data under consideration during their reconstruction to produce denoised experimental data. A selection criterion is based on the informative indicators quantifying the spatial information contained in images of scores associated with said principal components. The invention also provides for the capability to apply an adaptive filtering excluding the persistent spatial noise associated with each component selected.

15 Claims, 8 Drawing Sheets

(56) References Cited

FOREIGN PATENT DOCUMENTS

| JP | 2011-509697 A | 3/2011 | | |
|----|---|---|---|---|
| WO | 2009/073672 A1 | 6/2009 | | |
| WO | WO-2017183885 A1 | * | 10/2017 | ............. A61B 5/055 |

OTHER PUBLICATIONS

Lim, WO-2017183885A1 English Translation, Magentic Resonance Image Processing Apparatus and Image Processing Method Thereof (Year: 2017).*

Fortier, FR-2931935-A1 English Translation, Object of interest i.e. brain tumor, volume measuring method for use during MRI, involves displaying value of measured volume of object of interest on interface or stroing value of measured volume in memory (Year: 2009).*

Balvay et al., "Signal-to-Noise Ratio Improvement in Dynamic Contrast-enhanced CT and MR Imaging with Automated Principal Component Analysis Filtering", Radiology, Feb. 2011, vol. 258, No. 2, p. 435-446. (12 pages).

Office Action (Notice of Reasons for Refusal) issued on Jan. 7, 2025, in corresponding Japanese Patent Application No. 2023-577184 and English translation of the Office Action. (10 pages).

Breitling, et al., "Adaptive denoising for chemical exchange saturation transfer MR imaging", NMR in Biomedicine, Jul. 2016, vol. 32, Jun. 2019, pp. 1-14.

Cárdenas-Blanco, et al., "Noise in Magnitude Magnetic Resonance Images" Concepts in Magnetic Resonance Part A 32A (6): pp. 409-416.

Gavish, et al., "Optimal Shrinkage of Singular Values." IEEE Transactions on Information Theory 63 (4), Apr. 2017, pp. 2137-2152.

International Search Report (PCT/ISA/210) with translation and Written Opinion (PCT/ISA/237) mailed on Oct. 20, 2022, by the European Patent Office as the International Searching Authority for International Application No. PCT/FR2022/051278 (17 pages).

Kaiser, "The Varimax Criterion for Analytic Rotation in Factor Analysis." Psychometrika 23 (3), Sep. 1958, 187-200.

Ma, et al., "Denoise Magnitude Diffusion Magnetic Resonance Images via Variance-Stabilizing Transformation and Optimal Singular-Value Manipulation." NeuroImage 215, Jul. 2020, pp. 1-20.

Manjon, et al., "Diffusion Weighted Image Denoising Using Overcomplete Local PCA", PLOS ONE, Sep. 2013, vol. 8, No. 9, pp. 1-12.

Valle, et al., "Selection of the Number of Principal Components: The Variance of the Reconstruction Error Criterion with a Comparison to Other Methods." Industrial and Engineering Chemistry Research 38 (11), 1999, 4389-4401.

Veraart, et al., "Denoising of diffusion MRI using random matrix theory", Neuroimage, Aug. 2016, vol. 142, pp. 394-406.

Zhang, et al., "Joint image denoising using adaptive principal component analysis and self-similarity", Information Sciences, Aug. 2013, vol. 259, pp. 128-141.

* cited by examiner

METHOD FOR ATTENUATING THE NOISE IN IMAGES RESULTING FROM MULTIPLE ACQUISITIONS BY MAGNETIC RESONANCE IMAGING

The invention relates to a method for attenuating the noise in (or "denoising") images obtained by multiple acquisitions by means of an imaging device, for example a medical magnetic resonance imaging device.

Magnetic resonance imaging, also known by the abbreviation MRI, is based on an analysis of the response of a proton of a water molecule when it is excited in a magnetic field. This response depends on the environment of such a proton and makes it possible to differentiate between several types of tissues. A nuclear magnetic resonance imaging device 1 of an imaging analysis system S, as shown by way of non-limitative example in FIGS. 1 and 2, is generally used. This delivers a plurality of sequences of digital images 12 of one or more parts of the body of a patient, by way of non-limitative examples the brain, the heart, the lungs. For this purpose, said device 1 applies a combination of high-frequency electromagnetic waves to the part of the body under consideration and measures the signal retransmitted by certain atoms, such as, by way of non-limitative example, hydrogen for nuclear magnetic resonance imaging. The device thus makes it possible to determine the magnetic properties and, consequently, the chemical composition of the biological tissues and therefore their natures, in each elementary volume, which is commonly named voxel, of the imaged volume. The magnetic resonance imaging device 1 is controlled with the aid of a console 2. A user 6, for example an operator, practitioner or researcher, can thus choose commands 11 for controlling the device 1, on the basis of parameters or setpoints 16 entered by means of an input human-machine interface 8 of the analysis system. Such a human-machine interface 8 can consist for example of a computer keyboard, a pointing device, a touchscreen, a microphone or, more generally, any interface arranged to translate a gesture or an instruction given by a human 6 into control or configuration data. On the basis of information 10 produced by said device 1, a plurality of sequences of digital images 12 of a part of a human or animal body is obtained. Such information 10 or images 12 will be named "experimental data" without distinction.

The sequences of images 12 can optionally be stored within a server 3, i.e. a computer equipped with its own storage means, and constitute a medical file 13 of a patient. Such a file 13 can comprise images of different types, such as functional images highlighting the activity of the tissues or anatomical images reflecting the properties of the tissues. The sequences of images 12 or, more generally, the experimental data are analysed by a processing unit 4 arranged for this purpose. Such a processing unit 4 can, for example, consist of one or more microprocessors or microcontrollers implementing appropriate application program instructions loaded in storage means of the imaging analysis system S.

By "storage means" is meant any volatile, or advantageously non-volatile, computerized memory. Non-volatile storage is computerized memory the technology of which makes it possible to retain its data in the absence of an electrical power supply. It can contain data resulting from input entries, calculations, measurements and/or program instructions. The main non-volatile storage currently available is of the type capable of being written to electrically, such as EPROM (erasable programmable read-only memory) or also written to and erased electrically, such as EEPROM (electrically erasable programmable read-only memory), flash, SSD (solid-state drive), etc. Non-volatile storage is distinguished from the storage known as "volatile", from which the data are lost in the absence of an electrical supply. The main types of volatile storage currently available are RAM (random access memory, also named "read-write memory"), DRAM (dynamic random-access memory, needing to be regularly refreshed), SRAM (static random-access memory, needing to be refreshed in this way when there is a loss of electrical power), DPRAM or VRAM (particularly suitable for video), etc. Hereinafter, "data memory" can be volatile or non-volatile according to the targeted application.

The processing unit 4 includes means for communicating with the outside world in order to collect the images. Said communication means make it possible moreover for the processing unit 4 to ultimately deliver a depiction, for example graphic and/or audible, of an estimation or quantification of a biomarker worked out by said processing unit 4 on the basis of the experimental data 10 and/or 12 obtained by magnetic resonance imaging, to a user 6 of the imaging analysis system S by means of an output human-machine interface 5. Throughout the document, by "output human-machine interface" is meant any device, used on its own or in combination, making it possible to output or deliver a graphic, haptic or sound representation, or one which is more generally perceptible to humans, of a reconstructed physiological signal, in this particular case a biomarker, to a user 6 of a magnetic resonance imaging analysis system S. Such an output human-machine interface 5 can consist, non-exhaustively, of one or more screens, loudspeakers or other suitable alternative means. Said user 6 of the imaging analysis system S can thus confirm or invalidate a diagnosis, decide on a therapeutic action judged to be appropriate, go into more depth for research work, refine parameters for adjusting an item of measurement equipment, etc. Optionally, this user 6 can also configure the operation of the processing unit 4 or of the output human-machine interface 5, by means of operating and/or acquisition parameters 16. For example, it is thus possible to define display thresholds or to choose the estimated or quantified biomarkers, indicators or parameters for which it is desired to have a representation. For this purpose, the user makes use of the aforementioned input human-machine interface 8 or a second input interface provided therefor. Advantageously, the input 8 and output 5 human-machine interfaces can constitute only one and the same physical entity. Said input 8 and output 5 human-machine interfaces of the imaging analysis system can also be integrated in the acquisition console 2. There is a variant, described with reference to FIG. 2, for which an imaging system, such as described previously, moreover includes a pre-processing unit 7 for analysing the sequences of images 12, deducing therefrom experimental signals 15, and delivering these latter to the processing unit 4 which is thus relieved of this task.

Several two-dimensional images or three-dimensional volumes can be acquired with or without modification of the adjustments and the parameters of the medical imaging system S. For example, in order to study the reaction timing on the arrival of a contrast agent, it is possible simply to repeat the acquisition without modifying the adjustments and the parameters of said system. On the other hand, other imaging techniques need to modify said adjustments and/or parameters in order to sample the desired parameter space.

Among the techniques or procedures based on magnetic resonance imaging, chemical exchange saturation transfer (CEST) imaging is distinguished. Such a technique consists of applying a radiofrequency pulse according to different determined resonant frequencies ω, such that chemical species of interest reach a saturation state. Said determined resonant frequencies ω are in fact respectively associated with different chemical species of interest, such as, non-limitatively, the amide group (—NH), the amine group (—NH2) or the hydroxyl group (—OH). The labile hydrogen protons thereof, thus excited, are exchanged with non-excited hydrogen protons of water. Such an application of a radiofrequency pulse, at a determined resonant frequency ω other than the one, ω0, associated with water, repeated continually for a determined duration, for example a few seconds, leads to an accumulation of water saturation of a chemical species of interest. A concentration thereof can be measured indirectly by the decrease in the signal of water, the phenomenon called the "CEST effect", which is analysed in the form of a Z-spectrum. Such a decrease can be easily detected by rapid magnetic resonance imaging acquisition sequences such as, non-exhaustively, single shot echo-planar imaging. FIG. 3 shows, for a voxel V of interest, an example of a Z-spectrum in the form of a set of samples $Zi(\Delta\omega)$ (or data set) according to relative frequency shifts $\Delta\omega$ with respect to the frequency of water, such shifts $\Delta\omega$ being expressed in ppm. More specifically, said FIG. 3 shows different images M(−6 ppm), M(−3.5 ppm), M(0 ppm), M(3.5 ppm), M(6 ppm) corresponding to frequency shifts $\Delta\omega$ respectively equal to −6 ppm, 3.5 ppm, 0 ppm, 3.5 ppm and 6 ppm. It also shows an image M0 acquired for frequencies remote from the frequency of water. The $Z(\Delta\omega)$-spectrum, which can be described as "standardized", corresponds for a given voxel to the ratio $M(\Delta\omega)$ to M0, for frequency shifts comprised between −6 ppm and 6 ppm. When the samples $Zi(\Delta\omega)$ are ordered according to increasing $\Delta\omega$, as indicated in FIG. 3, said Z-spectrum can be described in the form of a discrete signal describing m measurements, advantageously standardized by a signal measured without radiofrequency saturation and expressed as percentages, of the magnitude of an experimental signal delivered by a measurement device 1 for an elementary volume of an organ. According to FIG. 3, this set of m samples, when these latter are ordered according to increasing frequency shifts $\Delta\omega$, constitutes a discrete Z signal substantially describing a 'V' the minimum $Zi(\Delta\omega)m$ of which is associated with the frequency shift $\Delta\omega=0$ ppm, when the device is perfectly adjusted and/or when the static magnetic field is homogenous.

The CEST technique improves the detection of certain metabolites of the human body, the concentration of which is insufficient to be detected by traditional magnetic resonance imaging sequences. This CEST technique thus makes it possible to obtain invaluable information for a practitioner seeking to establish a diagnosis and to make a therapeutic decision in the treatment of pathologies.

Diffusion tensor imaging (DTI) may also be mentioned, for which data are acquired for different intensities (b values) and directions of the magnetic diffusion gradient. This category includes perfusion weighted imaging (PWI) and two of its main techniques: dynamic susceptibility contrast (DSC) and dynamic contrast enhanced (DCE). There is also the high angular resolution diffusion imaging (HARDI) technique.

In magnetic resonance imaging, the signal induced in a receiving coil is a continuous complex signal, i.e. it includes a real part and an imaginary part, acquired within a frequency domain commonly called "k-space". The noise on such a signal can be described as a complex contribution, additional to and not correlated with said pure signal. Such a noise thus includes a real component and an imaginary component, independent of one another and distributed identically according to a Gaussian distribution with a zero mean and a standard deviation (cf. Cárdenas-Blanco et al. 2008; Aja-Fernández and Vegas-Sánchez-Ferrero 2016—technical teaching accessible for example via the hyperlink "https://doi.org/10.1007/978-3-319-39934-8"). However, in this field it is usual to consider magnitude images rather than said complex signal. Given that the transformation of the complex signal into a magnitude signal recorded in the magnitude images is non-linear, the distribution of the intensities of the pixels in the resulting images is generally not Gaussian and, under certain conditions, it can be modelled by a Rice distribution, as detailed in the document Cárdenas-Blanco, Arturo, Cristian Tejos, Pablo Irarrazaval, and Ian Cameron—2008, "Noise in Magnitude Magnetic Resonance Images" *Concepts in Magnetic Resonance Part A* 32A (6): 409-16, a document which can be consulted via the link "https://doi.org/10.1002/cmr.a.20124".

In the field of magnetic resonance imaging, it is known to reduce or eliminate noise in or from the experimental data (i.e. the measured data). The terms "to denoise" or "denoising" are used to describe this operation which consists of excluding or filtering noise in order to consider only the important items of information within said experimental data. To this end, there are numerous methods making use of principal component analysis (PCA).

Principal component analysis is a non-parametric technique (i.e. without reference to any model) originally designed to reduce the dimensions of a data set, while retaining the fundamentals of said data. Such an approach is disclosed for example in the document Jolliffe, I. 2002. "Principal Component Analysis" Second Edition, Springer-Verlag, accessible via the link "https://doi.org/10.1007/b98835". Such a method identifies and makes use of the linear correlations in the data under consideration and extracts therefrom a new non-correlated data set of smaller size, called "principal components". These principal components thus extracted are ordered as a function of the variability (or variances) that they express. Thus, the first principal components describe the most informative part of the data, concentrating most of the data variance.

In simple terms, applied to imaging, the aim of principal component analysis is to identify the most significant basis in order to "re-express" noisy experimental data and constitute a denoised experimental data set, i.e. for which the noise has been filtered so as to reveal one or more structures of interest that may have been masked by said noise.

From a geometric point of view, the problem of PCA can be simplified as follows: for a given collection of (real) points in a space having m dimensions, finding q vectors for which:

a $j^{th}$ vector represents a line of best fit through the points;
said $j^{th}$ vector being orthogonal to the j−1 vectors calculated beforehand.

By "best fit" is meant finding a line or axis that minimizes the average quadratic distance from the points to the line. Such a fit is shown in FIG. 4. In the left-hand part of this figure, a scatter plot can be seen, inscribed within a two-dimensional frame of reference or basis, shown by the axes x1 and x2. In the right-hand part, it can be seen that the axis z1 is the line of best fit through said points, the data or points being capable of being projected into a new frame of reference or basis described by the axis z1 and the axis z2 normal to z1. The principal component z1 is characterized by the greater variance $\lambda 1$ that is also named "eigenvalue" or "proper value". Thus, the set A of the respective eigenvalues A1 and A2 of the principal components z1 and z2 represents the quantities of items of information collected by said principal components or their respective informative capacities. The principal components z1 and z2 in FIG. 4 are named "eigenvectors" $\phi=\{\varphi 1, \varphi 2\}$ or "proper vectors".

Thus, a principal component analysis implies that:
the experimental data of dimension m can be expressed in the form of linear combinations of vectors;
the variance $\lambda$ of each principal component indicates significant items of information;
the q principal components, forming the new basis or the new frame of reference, are orthogonal.

FIG. 5 shows a known method for attenuating the noise in or "denoising" the experimental data in the form of standardized Z-spectra (each having m phases or frequencies) for a collection of n spatial sites (also called "voxels") of a human brain. Thus, for a given voxel, the experimental data are a vector having m acquisitions or samples. Such a method 100 includes:

a first step 110 of acquisition or collection of experimental data Z1 to Zn for a set of n voxels V1 to Vn having m different phases (or samples) from said voxel data in the form of a Casorati matrix C (matrix of n rows by m columns, for which each of the n rows contains m acquired values for a given voxel). The n rows are dedicated respectively to the different voxels of a segment or volume under consideration;

a step 120 for extracting or calculating the q=m principal components best describing this noisy experimental data set, in this case for a given voxel, the Zi-spectrum, such that:

$$Zi = Za + \sum_{j=1}^{q}(Zi - Za)\varphi_j^T \varphi_j$$

Za being the mean of the Zi-spectrum; to this end the following calculation is performed:

$$\text{cov}(C) = \Phi^T \Lambda \Phi$$

$\phi$ describing the eigenvectors (or proper vectors) of the principal components and $\Lambda$ their eigenvalues (or proper values); the q components, therefore their eigenvectors $\varphi 1$ to $\varphi q$, extracted or calculated, are classified or ordered generally according to their respective variances or eigenvalues. The variance of a principal component of eigenvector $\varphi j$ is described by a scalar value $\lambda j$, which is named "eigenvalue";

a step 130 of determining the optimal number k<q of principal components or, more specifically, of selecting the most significant or informative k components among the q components extracted, i.e. the k components describing items of spatial information of interest, as opposed to the q-k other components mainly describing noise, which should be discarded;

a step 140 of projecting the noisy experimental data onto the remaining k components to constitute a new denoised experimental data set, in this case in the example in FIG. 5, a Zi'-spectrum for a voxel of interest, such that:

$$Zi' = Za + \sum_{j=1}^{k}(Zi - Za)\varphi_j^T \varphi_j$$

a step 150 of reorganizing the denoised experimental data Z1' to Zn' in the origin space of the voxels V1 to Vn and making use of all or part of said denoised experimental data Z1', Zi', ..., to Zn' according to the chosen application.

By way of example, as indicated in FIG. 5, the noisy Zi-spectrum of a voxel under consideration appears, after such a method 100 has been implemented, in the form of a curve Zi' that is "smoother" than that described by the "raw" experimental data Zi.

The step 120 has been described according to a first embodiment on the basis of the covariance matrix. In a variant, such a production of q principal components can consist, according to a second embodiment, of singular value decomposition (SVD) of a Casorati matrix C as mentioned above. According to this second embodiment, an item of experimental data, for example in the form of a Zi-spectrum, for a given voxel can be expressed in the form:

$$Zi = Za + \sum_{j=1}^{q} t_{ij} v_j = Za + t_i V^t$$

where Za is the mean spectrum, i.e. the mean of the values in the $i^{th}$ row of the Casorati matrix C, $t_i$ is a vector of q coefficients, hereinafter named "scores", to describe the respective contributions of the principal components and $V^t$ is a matrix of q rows and q columns of said principal components. Thus, it is possible to rewrite the matrix C such that $C=TV^t+Za$, which is calculated on the basis of a singular value decomposition of the matrix C such that $C-Za=USV^t$ where U is a matrix of n rows and n columns describing the scores (or coefficients or also weights) of the principal components ($u_j$ describes the principal component scores of rank j), S is a matrix of n rows and q columns describing q non-zero values $S_1$ to $S_q$ called "singular values" and $V^t$ is a matrix of m rows and m columns describing the new basis of the principal components.

The singular values of the matrix S are classified in decreasing order. It is noted that if the matrix C is transposed, its rows describing m variables and its columns n samples, then the respective interpretations of the matrices U and V are interchanged.

By identifying the terms in the preceding equations, it is possible to deduce that T=US is a matrix of the scores of the principal components multiplied by singular values, $V^t$ being the matrix of the principal components. Such a second embodiment of step 120 is mainly focused on analysis of the spatial information contained in each column of the matrix U or, similarly, of the matrix T. As mentioned above, such a step 120 can be based on the covariance matrix $\text{cov}(C)=\Phi^T \Lambda \Phi$ for which $\Phi$ describes the eigenvectors of the principal components and $\Lambda$ their eigenvalues; the q components, therefore their eigenvectors $\varphi 1$ to $\varphi q$, extracted or calculated, are generally classified or ordered according to their respective variances or eigenvalues $\lambda j$. There is a direct relationship between the singular values according to the second embodiment and the eigenvalues according to the first embodiment obtained (i.e. on the basis of the covariance matrix) such that $$\lambda j = \frac{s_j^2}{n-1}.$$

In order to attenuate the noise in experimental data, in this case a noisy Zi-spectrum, said "denoised" item of experimental data is obtained by implementing the step 140 of projecting the noisy experimental data onto the k remaining components to constitute a new denoised experimental data set, in this case in the example in FIG. 5, a Zi'-spectrum for a voxel of interest, such that:

$$Zi' = Za + \sum_{j=1}^{k} t_{ij} v_j = Za + t'_i V''$$

for which ti' is a vector of k scores and $V''$ is a matrix of k rows and q columns of the principal components.

Among the steps of denoising by principal component analysis, step 130 of selecting the components is the most tricky. In order to obtain the items of spatial information hidden in the principal components, it is possible to remodel each principal component (i.e. the real values of the voxels projected onto an eigenvector) in its dimension of origin (i.e. in a volume or a slice) as shown in FIG. 6. Images PC1 to PC29 respectively associated with said principal components of ranks 1 to 29 describe the scores associated with the eigenvectors φ1 to φ29 for the set of voxels V1 to Vn under consideration according to the method used for production 120 of the principal components. Such scores correspond to the projection of the experimental data onto said twenty-nine principal components. For the sake of simplicity, the term "score" will be used to describe a contribution of a principal component, regardless of the method of production or extraction 120 of such a principal component. The principle of a principal component analysis, according to the state of the art, in a way amounts to seeking to best express the experimental signals or data of a set of voxels resulting from a multiple acquisition, in the form of linear combinations of principal components according to respective scores, said principal components being classified according to an order of predominance resulting directly from eigenvalues of said principal components or from singular values associated therewith. Thus, the image PC1 in FIG. 6 depicts, like an image of a slice of a human brain, the scores of the first principal component, in order to reconstitute the experimental curves (Zi-spectra for i comprised between 1 and n) for n voxels under consideration. Similarly, the image PC2 in FIG. 6 depicts, like an image of a slice of a human brain, the scores of the second principal component, in order to reconstitute the experimental curves of the voxels under consideration. In other words, the image PC2 in FIG. 6 depicts said experimental data Z1 to Zn projected onto the second principal component. The same applies to images PC3 to PC29 describing respectively the scores of the third up to the twenty-ninth principal component for the voxels under consideration. This FIG. 6 makes it possible to show the result of implementing step 120 described above. As can be seen with the naked eye, the first nine images PC1 to PC9 respectively associated with the principal components of ranks 1 to 9 appear to express, to a decreasing degree, a relevant item of spatial information, as opposed to the other images PC10 to PC29 respectively associated with the principal components of higher ranks, which no longer appear to indicate anything. Of course, the selection 130 of k significant principal components is not carried out with the naked eye but following an automated method.

The state of the art abounds with processes or methods using different models and mathematical hypotheses or statistics, combinations with other techniques and various criteria for determining an "optimal" sub-set of k components in numerous fields and applications. Among these, some have been used with success for the purposes of denoising or filtering in magnetic resonance imaging, by generally reconstructing the experimental data set using the informative components and excluding the components mainly associated with the noise. To this end, numerous approaches focused on the data have been proposed to determine the k principal components among q extracted principal components that it is appropriate to retain and q-k principal components to be excluded during the reconstruction of the experimental data to obtain denoised experimental data.

However, most of the selection criteria are based on the set A of the eigenvalues associated with the q principal components extracted, i.e. based on measurements of variances expressed by the original data set, component by component, or on the residuals, i.e. on the respective mathematical differences between the original data and the reconstructed data. In this respect, there may be mentioned non-exhaustively the document by Breitling, Johannes, Anagha Deshmane, Steffen Goerke, Andreas Korzowski, Kai Herz, Mark E. Ladd, Klaus Scheffler, Peter Bachert, and Moritz Zaiss—2019—"Adaptive Denoising for Chemical Exchange Saturation Transfer MR Imaging" NMR in Biomedicine, no. March 2019: 1-14, accessible through the link "https://doi.org/10.1002/nbm.4133", the document by Kaiser, Henry F. 1958 "The Varimax Criterion for Analytic Rotation in Factor Analysis." Psychometrika 23 (3): 187-200, accessible via the link https://doi.org/10.1007/BF02289233 or also the document by Valle, Sergio, Weihua Li, and S. Joe Qin. 1999 "Selection of the Number of Principal Components: The Variance of the Reconstruction Error Criterion with a Comparison to Other Methods." Industrial and Engineering Chemistry Research 38 (11): 4389-4401, accessible through the link https://doi.org/10.1021/ie990110i). These publications present methods based on the eigenvalues of the principal components relying on the criteria of Malinowsky, Nelson and Median, applied to the denoising of in vivo CEST magnetic resonance imaging data.

Other methods have been proposed for denoising experimental diffusion MRI data. Some of these methods are based on random matrix theory, as disclosed for example in the document by Veraart, Jelle, Dmitry S. Novikov, Daan Christiaens, Benjamin Ades-aron, Jan Sijbers, and Els Fieremans—2016—"Denoising of Diffusion MRI Using Random Matrix Theory." NeuroImage 142: 394-406, accessible via the link "https://doi.org/10.1016/j.neuroimage.2016.08.016". Other methods are based on shrinkage of the singular value as described in the document by Ma, Xiaodong, Kamil Ugurbil, and Xiaoping Wu—2020—"Denoise Magnitude Diffusion Magnetic Resonance Images via Variance-Stabilizing Transformation and Optimal Singular-Value Manipulation." NeuroImage 215 (July): 116852, accessible via the link "https://doi.org/10.1016/j.neuroimage.2020.116852" the mathematical principles of which are explained in the document by Gavish, Matan, and David L. Donoho—2017—"Optimal Shrinkage of Singular Values." IEEE Transactions on Information Theory 63 (4): 2137-52, accessible via the link "https://doi.org/10.1109/TIT.2017.2653801").

Like the known method shown in FIG. 5, most of the methods proposed in the literature are based on the eigenvalues A in order to determine the k components to be retained and those to be excluded during the reconstruction of the data. Thus, as suggested in FIG. 5, a step 130 consists of comparing, in this case by means of a logarithmic scale, the eigenvalues $\lambda j$ of the q principal components, j being comprised between 1 and q. Below a certain predetermined variance threshold, the principal components are considered as expressing little or no relevant items of information and are excluded. Only the first k principal components, i.e. those of which the variances or eigenvalues are greater than said threshold, are retained for use in step 140. These methods have a major drawback, since they generally lead to disregarding hidden anatomical structures and items of pathological information in some discarded principal components. This drawback results directly from the use, as main selector, of the eigenvalues that are measurements of variance of the different principal components, blindly measuring the noise and the relevant items of information. The principal component analysis generally starts from the principle according to which the variance indicates the presence or absence of important items of information, which assumes that the experimental data analysed have a high signal-to-noise ratio, i.e. that the power of the signal of interest is greater than the power of the noise. This is a powerful and sometimes incorrect hypothesis, in particular for particularly noisy experimental magnetic resonance imaging data. Such a situation arises, for example, when the noise level in the experimental data delivered by a magnetic resonance imaging device is high, or when the signals of interest concern an anatomical or pathological area that is small with respect to the size of the images under consideration. Most of the methods proposed in the literature, based on the eigenvalues, thus discard principal components containing hidden anatomical structures or items of pathological information of interest, since the contributions of these areas to the eigenvalues of the associated components are small. Thus, a non-negligible quantity of relevant items of information is lost, since it is amalgamated with the noise according to the state of the art. Selecting the principal components cannot be carried out according to such criteria, which could be described as simplistic or trivial, in order to guarantee relevant use of the experimental data and deliver reliable indicators or biomarkers on the basis of denoised experimental data, as can be seen with reference to FIG. 12 by way of example.

The invention responds to the drawbacks raised by the state of the art. Among the numerous advantages achieved by the invention, there may be mentioned more particularly that a denoising method according to the invention includes a step of selecting the principal components making it possible to obtain a better compromise between efficiency of denoising and retention of the relevant items of spatial information of the experimental data under consideration during their reconstruction in order to produce denoised experimental data. By way of example, a proposed selection criterion is based on the decrease of the variance of an image having a score associated with a principal component after application of a smoothing filter thereto. This technique makes it possible to make use of the hidden spatial information, in particular the anatomical structures and the items of pathological information, in all the principal components extracted or calculated, and makes it possible to select those making it possible to express important items of information, independently of one another and of their ordering resulting from their extraction or production, thus minimizing the risk of excluding relevant principal components. The invention also makes it possible to have available a filtering step that can be described as adaptive, i.e. making it possible to further denoise the experimental data under consideration, while excluding the persistent spatial noise associated with each principal component extracted, while also adapting the level of filtering of the principal components to the quantity of relevant items of information that each one of them makes it possible to express.

To this end, the invention provides a method for attenuating the noise in experimental data originating from multiple acquisitions by an imaging device pertaining to an elementary volume of interest, hereinafter named "voxel" of interest, among a plurality of voxels, said method being implemented by a processing unit of a medical imaging analysis system. Such a method includes:
- a step of collecting said experimental data pertaining to the plurality of voxels;
- a step of projecting the experimental data into a base of functions or vectors producing a set of q components as well as their respective scores for the plurality of voxels, said scores corresponding to the projection of said experimental data onto said q components;
- a step of selecting first k components among the q components produced;
- a step of projecting said experimental data onto the k components selected and of producing noise-attenuated experimental data pertaining to the elementary volume of interest.

In order to optimize the denoising of the experimental data without loss of the spatial information, the step of selecting k components of such a method includes:
- a sub-step of producing score images of the components for the plurality of voxels and informative indicators quantifying the spatial information contained in said images of the scores associated with said components in the form of a rate of decrease of the values of a determined characteristic of said scores before and after application of a smoothing filter to said scores, said determined characteristic of the scores for a plurality of voxels belonging to a set of characteristics, alone or in combination, including variance, standard deviation, median and mean;
- a sub-step of determining the k components on the basis of said informative indicators produced.

According to an advantageous embodiment, the step of producing q components as well as their respective scores for the plurality of voxels can produce an ordered set of q principal components according to a determined order relation. The sub-step of determining the k components then consists of determining the rank k in order to select the first k principal components on the basis of said informative indicators produced.

According to this embodiment, the step of producing q components as well as their respective scores for the plurality of voxels can consist of implementing a principal component analysis to produce an ordered set of q principal components according to their respective eigenvalues.

In a variant, when the experimental data pertaining to the plurality of voxels result from a multiphase diffusion imaging acquisition by a magnetic resonance imaging device, said step of producing q components as well as their respective scores for the plurality of voxels can consist of implementing a spherical harmonic decomposition.

In a variant, when said experimental data pertaining to the plurality of voxels result from a multiphase acquisition by a functional magnetic resonance imaging device, said step of producing q components as well as their respective scores for the plurality of voxels can consist of implementing a Fourier transform decomposition.

When the set of the q components produced is ordered according to a determined order relation, the sub-step of determining the rank k can consist of calculating the mathematical difference between values of said informative indicators when these latter are ordered in accordance with the q components produced, the rank k being that of the principal component for which said mathematical difference falls below, or becomes equal to, a determined threshold.

In a variant, such a sub-step of determining said rank k can consist of detecting a plateau described by the values of the informative indicators when these latter are ordered in accordance with the q components produced, from the informative indicator of the component of rank q to the informative indicator of the component of rank 1, the rank k being that of the first component the value of the informative indicator of which deviates from said plateau.

When the indicators are ordered according to a determined order relation specific to them, said sub-step of determining the k components can consist of calculating the mathematical difference between successive values of said informative indicators, the k components selected being those for which said mathematical difference between the values of their informative indicators remains above a determined threshold. Such a sub-step of determining the k components could consist of detecting a plateau described by the values of said informative indicators, the k components selected being those for which their respective informative indicators deviate from said plateau.

In order to reinforce the weight of the predominant components during the reconstruction of the experimental data thus denoised, the step of selecting k components of a method according to the invention can include a sub-step of applying a filtering operation of the k components selected, the filtering intensity of which is specific to each of the k components selected and proportional to the informative indicator thereof.

In this case, the filtering operation can consist of the use, alone or in combination, of a Gaussian filter, a mean filter, a median filter, an anisotropic diffusion filter.

According to a second aspect, the invention relates to a computer program product including one or more program instructions that can be interpreted by the processing unit of a medical imaging analysis system, said program instructions being capable of being loaded in non-volatile storage of said medical imaging analysis system, the execution of said instructions of which by said processing unit causes the implementation of a method for attenuating the noise in experimental data according to the invention.

According to a third aspect, the invention relates to a computer-readable storage medium including the instructions of such a computer program product according to said invention.

According to a fourth aspect, the invention relates to an imaging analysis system including a processing unit arranged to attenuate the noise in experimental data originating from multiple acquisitions by an imaging device pertaining to an elementary volume of interest, hereinafter named "voxel" of interest, among a plurality of voxels, said processing unit being configured for:
  collecting said experimental data pertaining to the plurality of voxels;
  projecting the experimental data into a base of functions or vectors and producing a set of q components as well as their respective scores for the plurality of voxels, said scores corresponding to the projection of said experimental data onto said q components;
  selecting k components among the q components produced;
  projecting said experimental data onto the k components selected and producing noise-attenuated experimental data pertaining to the elementary volume of interest.

In order to optimize the denoising of the experimental data without loss of spatial information, the processing unit of such a system is configured for:
  producing score images of the components for the plurality of voxels and informative indicators quantifying the spatial information contained in said images of the scores associated with said components in the form of a rate of decrease of the values of a determined characteristic of said scores before and after application of a smoothing filter to said scores, said determined characteristic of the scores for a plurality of voxels belonging to a set of characteristics, alone or in combination, including variance, standard deviation, median and mean;
  selecting the k components on the basis of said informative indicators produced.

According to an advantageous embodiment, such an imaging analysis system can include a program memory including the program instructions of a computer program product according to the invention.

Other characteristics and advantages will become more clearly apparent on reading the following description and on examining the figures which accompany it, in which:

FIG. 1, already described, shows a simplified depiction of a system for analysing images obtained by magnetic resonance;

FIG. 2, already described, shows a simplified depiction of a variant of a system for analysing images obtained by magnetic resonance;

FIG. 3, already described, shows an example of a Z-spectrum in the form of a set of samples $Zi(\Delta\omega)$ according to relative frequency shifts $\Delta\omega$ with respect to the frequency of water, such shifts $\Delta\omega$ being expressed in ppm;

FIG. 4, already described, shows the principle of principal component analysis consisting of transforming variables or data associated with one another (also described as "correlated" in statistics) into new variables or data that are decorrelated from one another;

FIG. 5, already described, shows a known method for denoising a noisy Zi-spectrum resulting from a CEST acquisition according to the state of the art;

FIG. 6, already described, shows the experimental data projected onto different principal components extracted from a CEST data set after remodelling in their origin space;

Figure 1:
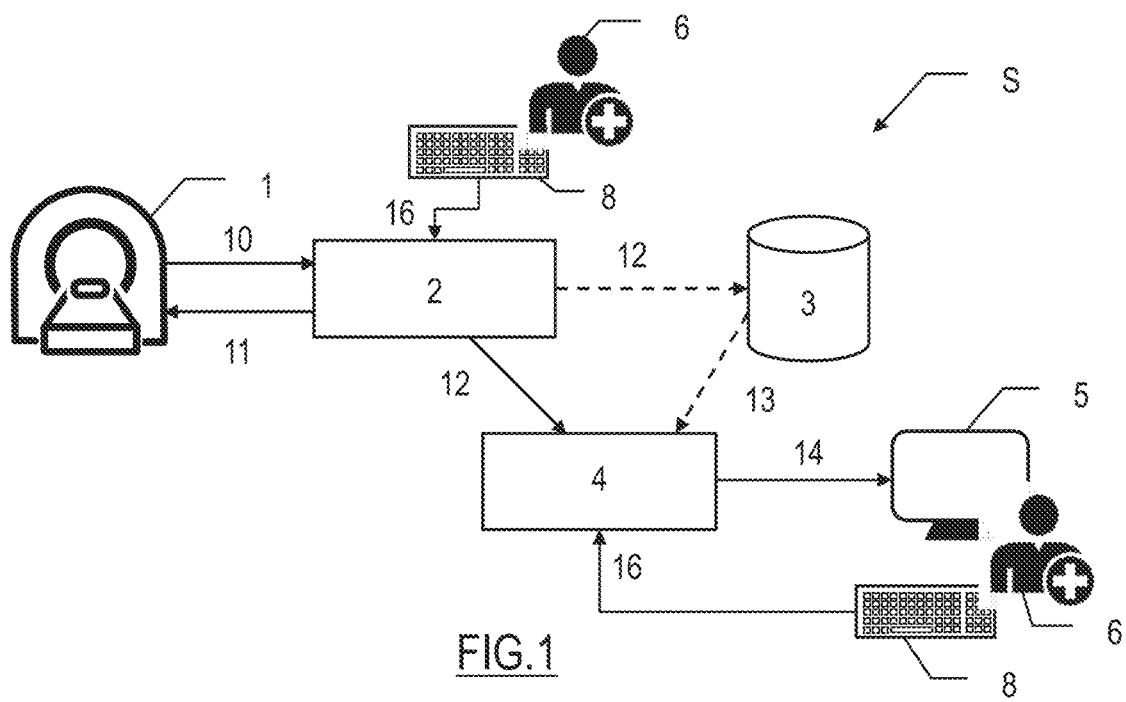
Figure 2:
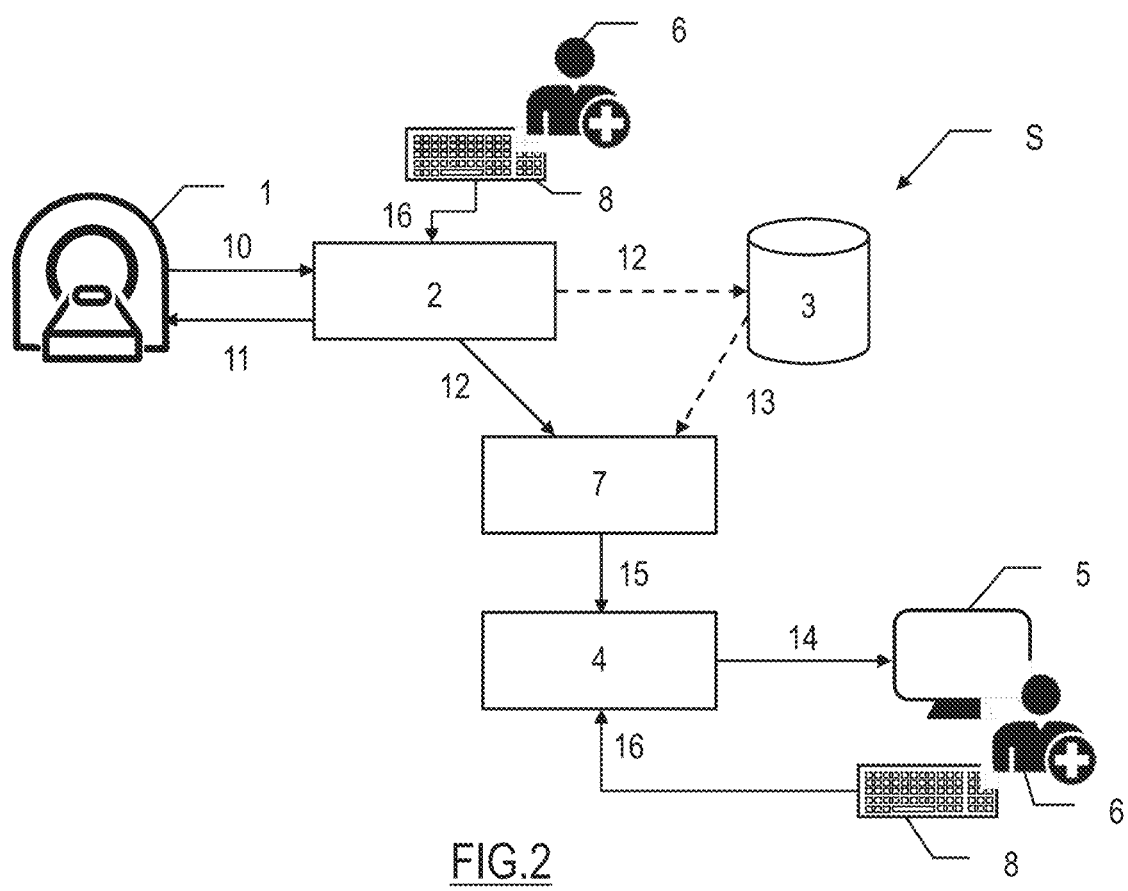
Figure 7:
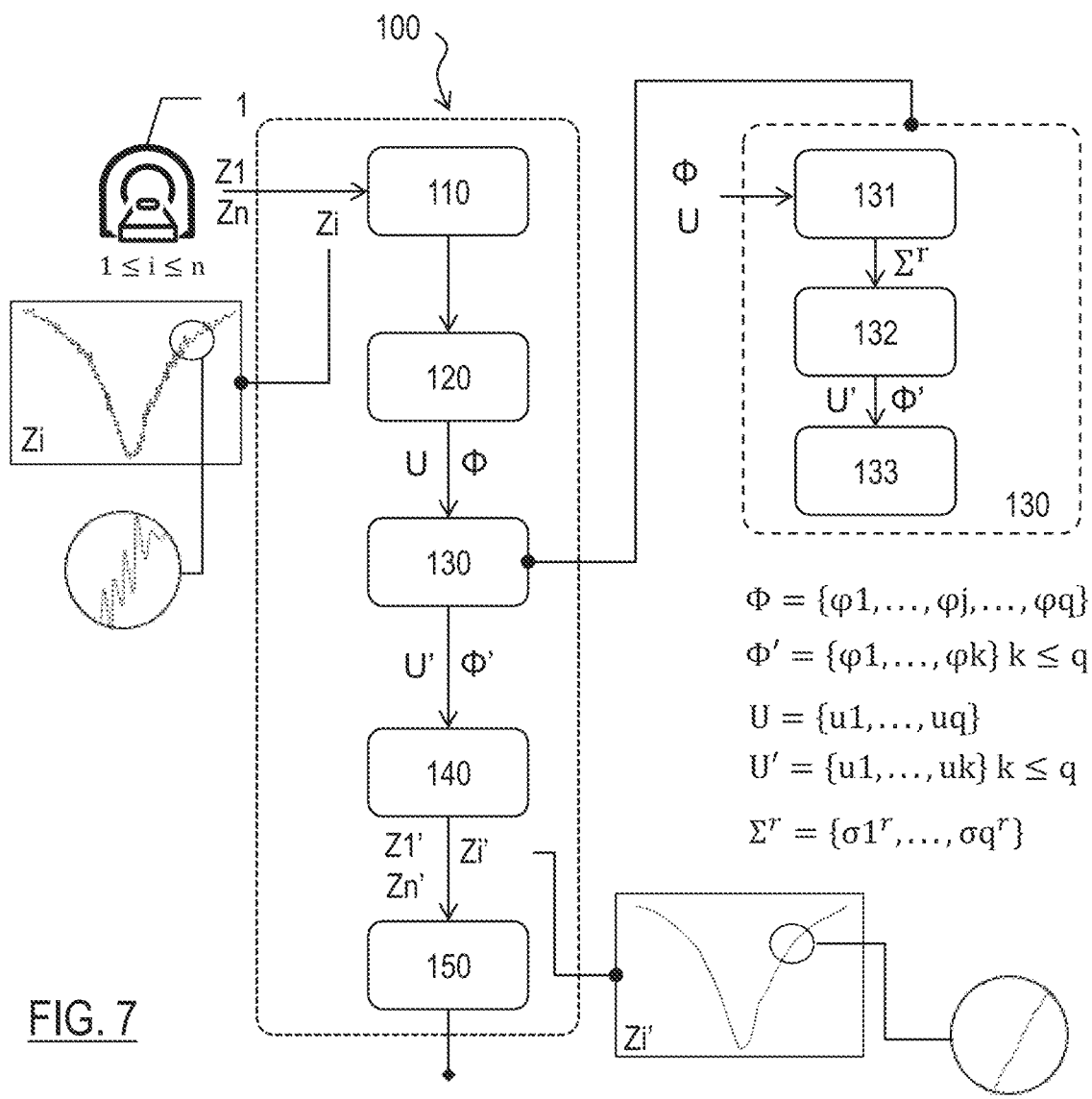
FIG. 7 shows an example functional algorithm of a denoising method according to the invention.

A method 100 for attenuation of the noise in medical images, according to the invention and shown in FIG. 7, is advantageously expressed in the form of a computer program product the program instructions of which are intended to be installed in the program memory of an element of a medical imaging system, such as the system S in FIGS. 1 and 2, for example a computer or a computer system server or, more generally, any electronic object having a sufficient computation power available.

Figure 3:
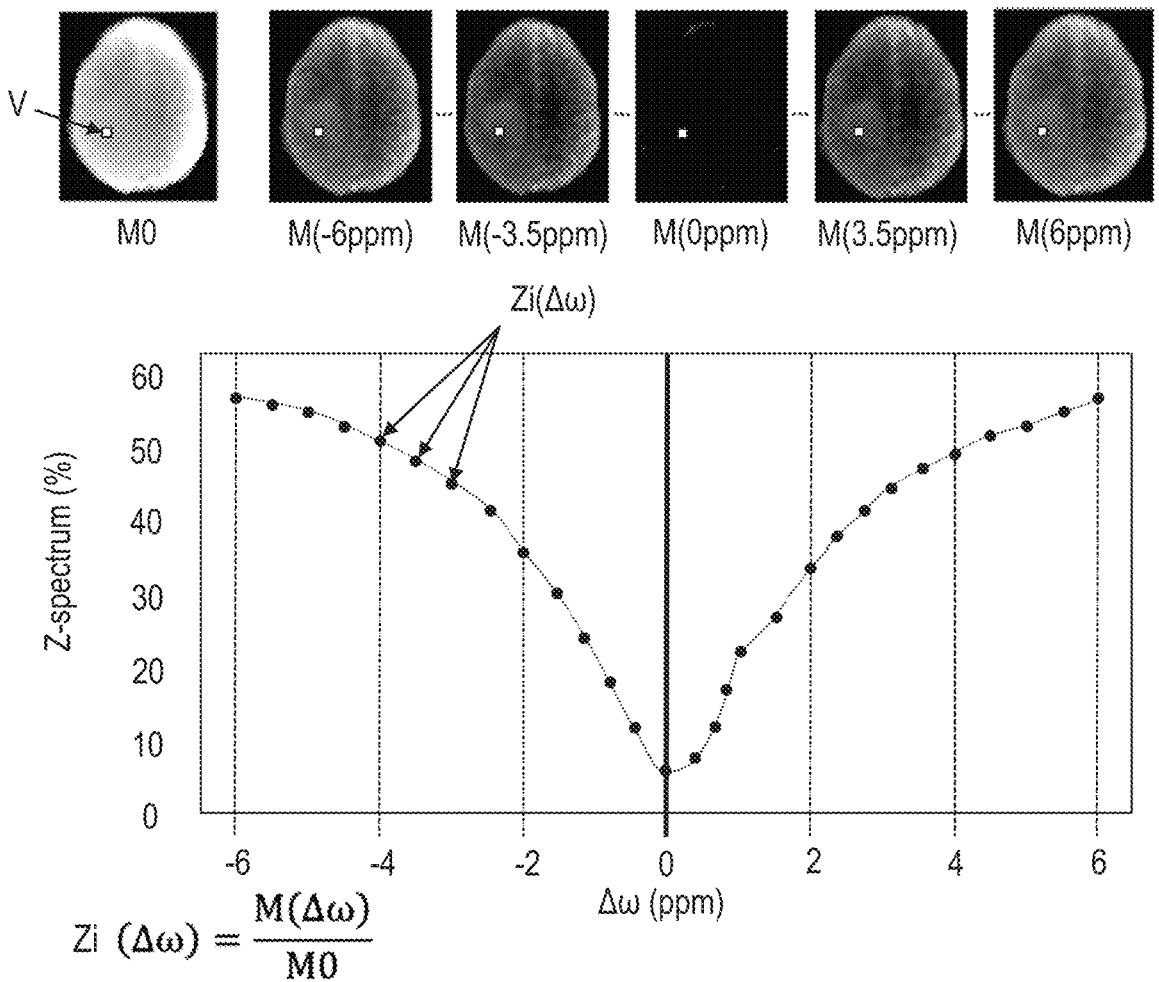
Figure 4:
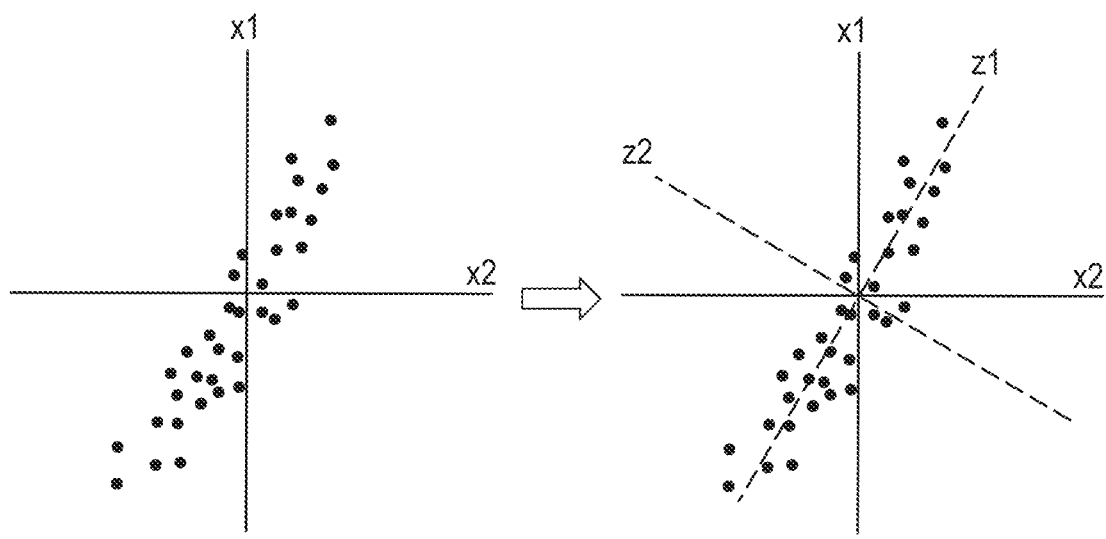

FIG. 7 thus shows a method 100, according to the invention, for attenuation of the noise in experimental data originating from multiple acquisitions by an imaging device, for example a magnetic resonance imaging device, such as the device 1 of the medical analysis system S shown in FIGS. 1 and 2, pertaining to a plurality of n voxels. Such a method includes some common steps with the method 100 according to FIG. 5. Thus, a "denoising" method 100 according to the invention can include, if necessary, a step 110 of collection or acquisition of noisy experimental data pertaining to or concerning said plurality of voxels V1 to Vn. Such experimental data can consist of curves such as Z1- to Zn-spectra following an acquisition of the CEST type, like the example referenced in FIGS. 3 and 5 or, more generally, any experimental data for a set of voxels or pixels pertaining to a volume or a slice of an organ concerned by a plurality of m acquisitions according to different instants or different phases for example. Such experimental data could thus, non-exhaustively, result from a multiphase high angular resolution diffusion imaging (HARDI) acquisition, concern the field of perfusion imaging by scanning or magnetic resonance imaging.

Figure 5:
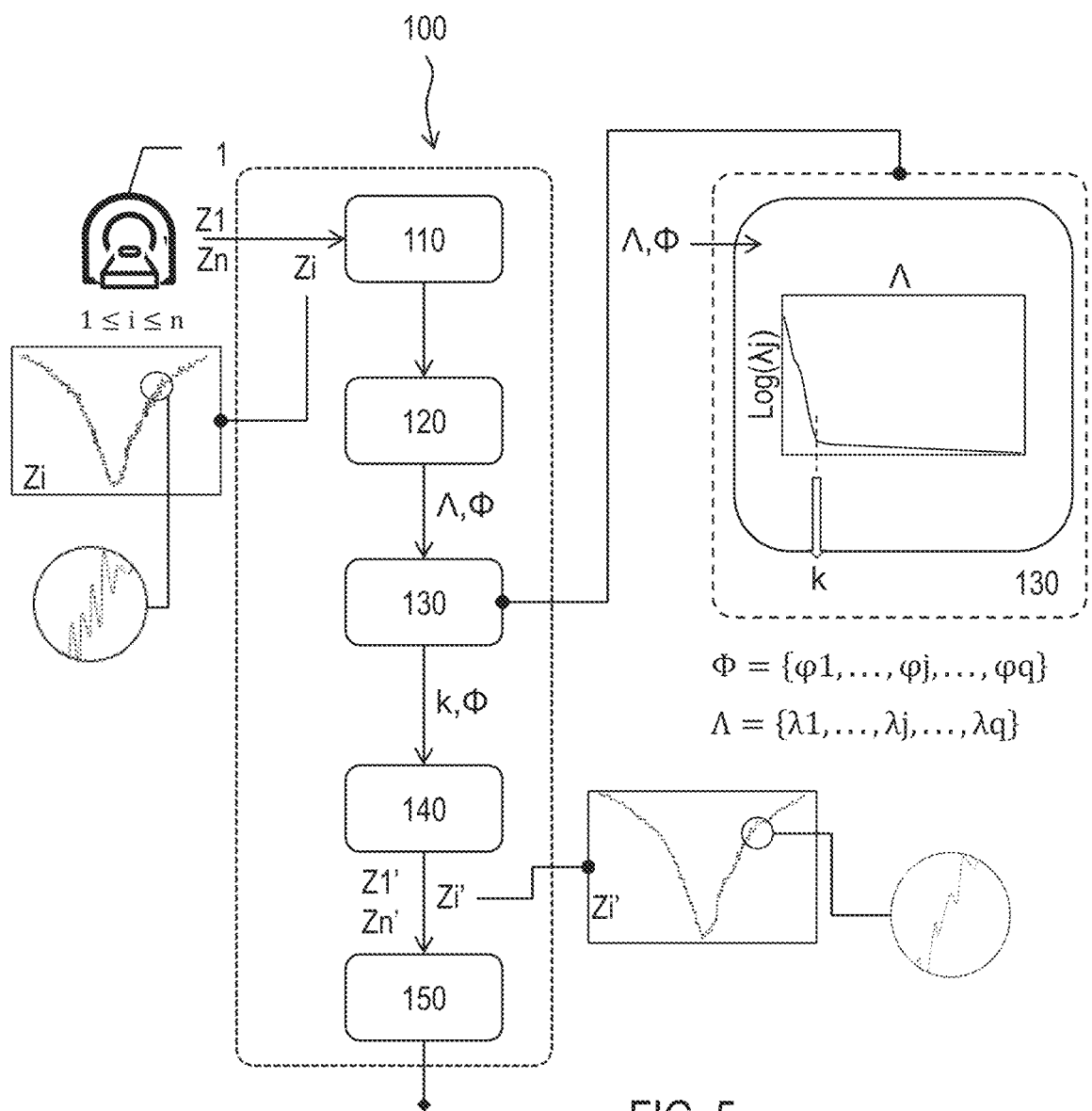

By way of preferred but non-limitative example, like FIG. 5, FIG. 7 depicts experimental data Zi pertaining to a voxel of interest among the n voxels acquired. FIG. 7 shows experimental data Zi, in the form of a noisy spectrum identical to that shown in FIG. 5. Such a noise is expressed by more or less pronounced discontinuities or oscillations according to the frequency shifts concerned, as evidenced by the partial enlargement of said Zi-spectrum. In order to attenuate this phenomenon, like the known method 100 and shown in FIG. 5, a method 100 according to the invention includes a step 120 of implementing a principal component analysis to produce or calculate q principal components, said step being similar to step 120 of the known method 100 according to FIG. 5. Such a step 120 consists of determining q principal components respectively symbolized by or associated with eigenvalues $\lambda 1, \ldots, \lambda q$ or with singular values $s_1$ to $s_q$ forming an ordered set of principal components the rank of which is determined according to a set of decreasing scalar values, such as the eigenvalues $\Lambda = \{\lambda 1, \ldots, \lambda q\}$ or the singular values S. In a variant, such principal components could be ordered according to any other order relation or even not be ordered. Such a method 100 according to the invention also includes a step 130 of determining or selecting k principal components among the q produced, i.e. the principal components of ranks 1 to k when these latter are ordered according to a determined order relation, to determine a smaller set of principal components. The selection 130, according to the invention and shown in FIG. 7, is clearly differentiated from the approach described in the great majority in the state of the art based on eigenvalues A. Such a step 130 specific to the invention will be detailed hereinafter. A method 100 according to the invention also includes, like the known methods 100 as shown in FIG. 5, a step 140 of projecting the noisy experimental data Zi onto the k principal components selected in step 130 and producing noise-attenuated, or "denoised", experimental data Zi' pertaining to an elementary volume of interest. It is possible to observe the increased efficiency of a method 100 according to the invention, by virtue of an improved selection, or a modification of the k principal components, prior to said projection 140, by examining the denoised Zi'-spectrum describing a particularly smooth curve with respect to the one described by the Zi-spectrum of origin. Like the one shown in FIG. 5, step 140 of the method 100 according to the figure consists of projecting the noisy experimental data set Z1, ..., Zi, ..., Zn onto the k principal components selected, and producing noise-attenuated experimental data Z1', ..., Zi', ..., Zn' for the voxels of interest V1 to Vn. Thus, optionally and advantageously, such a method 100 according to the invention can include a step 150 of joint use of the denoised experimental data Z1', ..., Zi', ..., Zn' for all or part of a plurality of said voxels of interest V1 to Vn. Such a use can for example consist of counting fibres in tractography on the basis of HARDI diffusion experimental data, as will be discussed with reference to FIGS. 10 to 12.

In a variant, step 120 for producing a set of q components can result from the implementation of techniques other than principal component analysis. Such a step 120 consists more generally of a decomposition or projection of the signal or of the experimental data into a base of functions or vectors. Thus, such a step 120 can consist for example, when the experimental data result from a multiphase diffusion imaging acquisition by a magnetic resonance imaging device, of implementing a spherical harmonic decomposition. Similarly, such a step 120 could, instead of principal component analysis, consist of implementing a Fourier transform decomposition, for example by Fast Fourier Transformation, of experimental data resulting from a multiphase acquisition by a functional magnetic resonance imaging device, a technique also known as fMRI.

Figure 8:
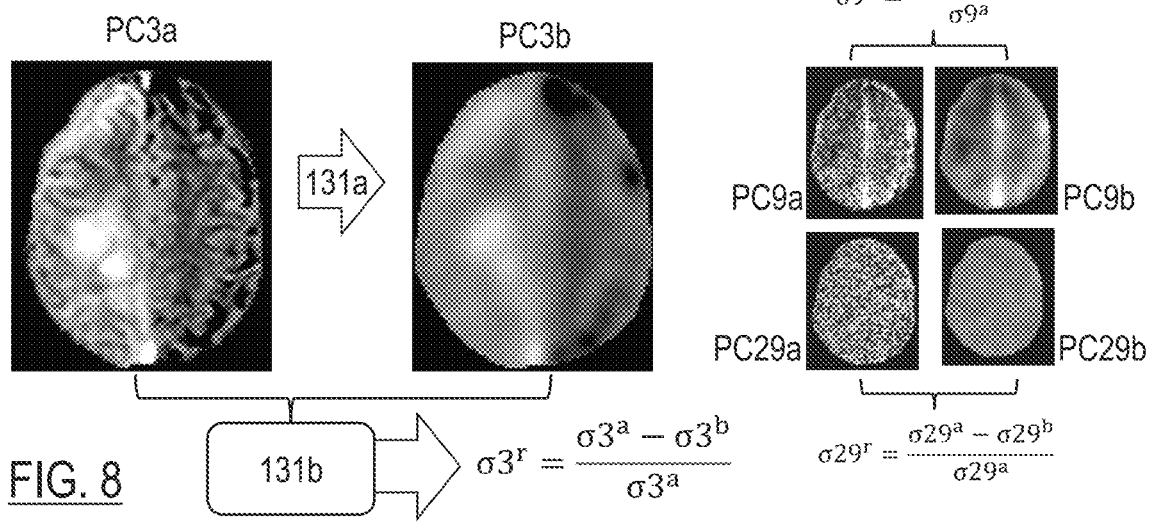
FIG. 8 shows an example calculation of a principal component informative indicator specific to the invention.

The invention is thus differentiated mainly by the implementation of step 130 making it possible to select the relevant components, i.e., making it possible to optimize the attenuation of the noise without losing relevant items of spatial information. Thus, as shown in FIG. 7, such a step 130 includes a sub-step 131 of producing informative indicators, referenced $\sigma 1^r, \ldots, \sigma q^r$ in FIG. 7, calculated respectively for the q principal components produced of ranks 1 to q in step 120 when the latter consists of a decomposition by principal component analysis. Such a set $\Sigma^r$ of informative indicators $\sigma 1^r$ to $\sigma q^r$ is an alternative to the set $\Lambda$ of the eigenvalues $\lambda 1$ to $\lambda q$ used directly by the known methods for selecting k principal components among the q extracted. Such an informative indicator $\sigma j^r$ characterizes the capacity of a principal component of rank j to express relevant spatial information. It can advantageously consist of a rate of decrease of the values of a determined characteristic of the scores of said principal component pertaining to the plurality of voxels V1 to Vn under consideration or of interest, before and after application of a smoothing filter to said scores. Such an operation 131a is shown in FIG. 8. This depicts, for the principal component of rank 3, two images PC3a and PC3b showing the scores of said principal component of rank 3 for the set of voxels under consideration. The image PC3a depicts said scores before application 131a of a smoothing filter and the image PC3b depicts these same scores after said application 131a of the smoothing filter.

This latter thus appears more blurred with respect to the image PC3a in FIG. 8. Such an operation 131*a* can advantageously consist of applying a Gaussian filter of Factor F having a predetermined value, optionally configurable.

By way of preferred but non-limitative example, said determined characteristic can consist of the standard deviation of said scores. The informative indicator σj$^r$ of a principal component of rank j can then be calculated in an operation 131*b* such that:

$$\sigma j^r = \frac{\sigma j^a - \sigma j^b}{\sigma j^a}$$

where σj$^a$ is the standard deviation of the scores of the principal component of rank j before application 131*a* of the smoothing filter and σj$^b$ is the standard deviation of said scores after application 131*a* of said smoothing filter.

In this case, in FIG. 8, the informative indicator σ3$^r$ of the principal component of rank 3 is such that:

$$\sigma 3^r = \frac{\sigma 3^a - \sigma 3^b}{\sigma 3^a}$$

Similarly, FIG. 8 shows the calculation of the informative indicator σ9$^r$ of the principal component of rank 9 is such that:

$$\sigma 9^r = \frac{\sigma 9^a - \sigma 9^b}{\sigma 9^a}$$

or also of the informative indicator σ29$^r$ of the principal component of rank 29 is such that:

$$\sigma 29^r = \frac{\sigma 29^a - \sigma 29^b}{\sigma 29^a}$$

In this way, the set Σr of the informative indicators of the q principal components of ranks 1 to q produced in step 120 and ordered according to their respective eigenvalues A or singular values S can be constituted at the end of implementation of the sub-step 131. In a variant, this set Σr of the informative indicators of the q principal components can be ordered according to the numerical values of said informative indicators or according to any other order relation.

In a variant or in addition, such a determined characteristic σjr could, instead of standard deviation, make use of the variance, entropy, median or also the mean of said scores of the principal component of rank j, or also result from a combination of all or some of these.

Figure 6:
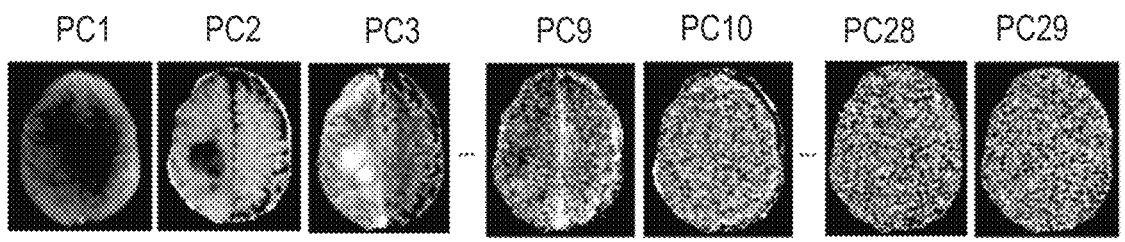
Figure 9:
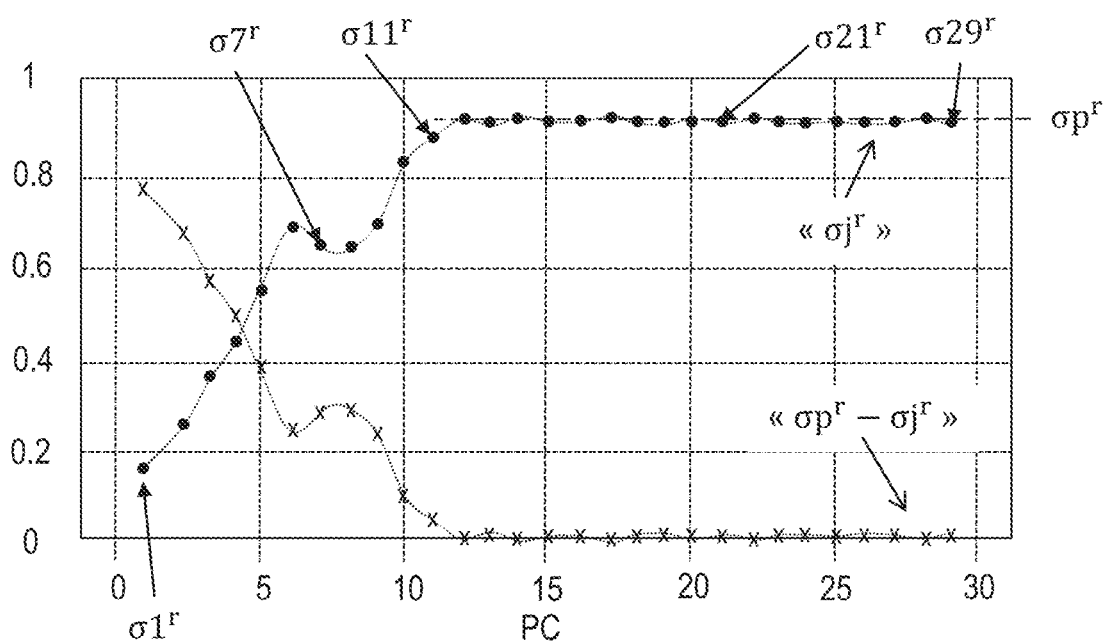
FIG. 9 shows an example selection of principal components according to the invention.

Once the set $\Sigma^r$ of the informative indicators has been calculated, step 130 of a method 100 according to the invention includes a sub-step 132 of determining the rank k in order to select the first k principal components (symbolized by the set of eigenvectors φ'={φ1, ..., φk} or the matrix U'={$u_1$, ..., $u_k$} in FIG. 7) on the basis of said set $\Sigma^r$ of said informative indicators. The implementation of such a sub-step 132 is shown in FIG. 9. The latter shows, with reference to the q=29 principal components of ranks 1 to 29, the scores PC1 to PC29 of which for a plurality of voxels of interest are shown in FIG. 6, the set $\Sigma^r$ of the informative indicators calculated in 131*b* and ordered according to the respective ranks of the q=29 principal components produced in step 120. The values of said informative indicators describe a curve "σj$^r$" substantially increasing when the rank of the principal components increases, to reach a plateau σp$^r$ of the order of ninety percent in the example shown in FIG. 9 starting from rank 12. The value of convergence or of a plateau σp$^r$ depends on the power of the smoothing that was applied to the score images in FIG. 8 and on the characteristic used to produce the informative indicators. As previously noted with reference to FIG. 6, the component of rank j=1 seems to express more items of spatial information than the components of ranks j greater than 10. Step 132 thus makes it possible, according to different embodiments, to objectivize the selection of the first k principal components in order to obtain the compromise sought. Thus, according to a first embodiment, such a sub-step 132 can consist of calculating the mathematical difference between values of said informative indicators $\Sigma^r$={σ1$^r$, ..., σq$^r$} when these latter are ordered in accordance with the ranks j of the q principal components produced. The rank k can be determined based on such a difference between two informative indicators of consecutive ranks. Thus, as soon as said difference falls below, or becomes equal to, (in absolute value) a determined threshold, for example a threshold of a value below three hundredths, the rank k sought is that of the principal component of the rank immediately below that of the principal component for which the informative indicator is substantially equal (difference substantially zero or below said threshold) to that of the principal component of the rank which is immediately above it. Such an approach is relevant when the informative indicators, ordered according to the ranks of the principal components that are respectively associated therewith, describe a curve "σj$^r$" that is substantially increasing until reaching a plateau σp$^r$. In a variant or in addition to the calculation of a mathematical difference between two informative indicators of consecutive ranks, the invention provides for the possibility of calculating a mean mathematical difference between an enhanced collection of consecutive indicators, a difference between the informative indicators of rank(s) lower and/or higher than a given informative indicator or any other equivalent technique. However, as indicated by the curve "σj$^r$" shown in FIG. 9, the latter can have one or more level sections. In this case, a first level section is depicted by the values of the informative indicators σ7$^r$ and σ8$^r$ of the principal components of ranks 7 and 8. A second level section is depicted by the values of the informative indicators σ12$^r$ to σ29$^r$ of the principal components of ranks greater than or equal to 12. So as not to determine a rank k that is too low pertaining to the existence of an intermediate level section for which the derivative of the curve "σj$^r$" is substantially zero, such a calculation of the derivative can be accompanied by or combined with the calculation of a deviation (depicted by the curve "σp$^r$-σj$^r$" in FIG. 9) with the informative indicator associated with the principal component of the highest rank, in this case the rank q=29, or the informative indicator of maximum value. If said deviation "σp$^r$-σj$^r$" is very low (for example less than three hundredths), then step 132 considers that the curve has reached the asymptote or the plateau σp$^r$. The rank k is thus determined as being that of the principal component of the rank immediately below. This is for example the case of the component of rank k=11, which is the last having an informative indicator σ11$^r$ "escaping" the plateau σp$^r$ or, more specifically, the value of which deviates substantially from the value σp$^r$ of said plateau. On the other hand, if said deviation "σp$^r$-σj$^r$" is significant, for example greater than ten percent of the value $\bar{\sigma}p^r$, (the case of the principal component of rank 7 the informative indicator $\bar{\sigma}7^r$ of which is substantially equal to that, $\bar{\sigma}8^r$, of the principal component of the rank immediately above in the example shown in FIG. 9), then such a level section of the curve "$\bar{\sigma}j^r$" is disregarded.

In a variant, such a sub-step 132 can consist of the detection of a plateau $\bar{\sigma}p^r$, as mentioned above, described by the values of the informative indicators $\bar{\sigma}j^r$ (j being comprised between 1 and q), passing through these latter from the highest rank of the principal components, in this case the rank q=29, to the rank 1. By assumption, such a plateau $\bar{\sigma}p^r$ exists for the principal components of the highest ranks, in this case in FIG. 9, the plateau $\bar{\sigma}p^r$ is of the order of ninety percent. The rank k sought is determined as being that of the first principal component the value of the informative indicator $\bar{\sigma}k^r$ of which deviates significantly from said plateau $\bar{\sigma}p^r$ (i.e. beyond a predetermined threshold, for example five percent of the value of said plateau). In this case, the informative indicator $\bar{\sigma}11^r$ is the first to describe such a value sufficiently distinct from the value of said plateau $\bar{\sigma}p^r$. The rank k sought is thus that of said principal component of rank k equal to eleven.

The invention is not to be considered limited by such operations implemented within the context of the sub-step 132 for detecting the value of the rank k on the basis of the ordered set of the informative indicators $\Sigma^r$.

As mentioned above, the informative indicators of the components can be ordered according to an order relation independent of the ranks or an ordering according to an order relation specific to the components produced. In this case, the sub-step 132 of determining k components can consist of calculating the mathematical difference between successive values of said informative indicators of the components and selecting only the k components the mathematical difference of which between the values of their respective informative indicators remains above a determined threshold. Similarly, according to this variant according to which the informative indicators of the components are ordered according to an order relation specific to them, the sub-step 132 can consist of selecting the k components for which their respective informative indicators deviate from a plateau such as the aforementioned plateau $\bar{\sigma}p^r$.

Figure 15:
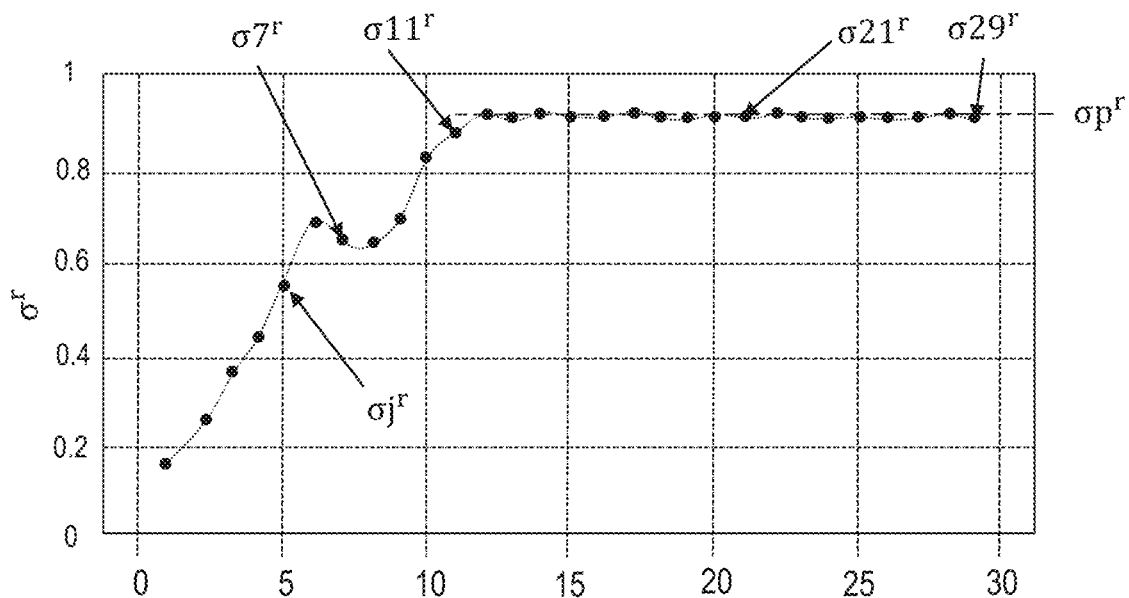
FIG. 15 shows an advantageous embodiment of a method according to the invention making it possible to adjust the weights specific to the different principal components selected prior to the projection of the noisy experimental data onto them.
Figure 15:
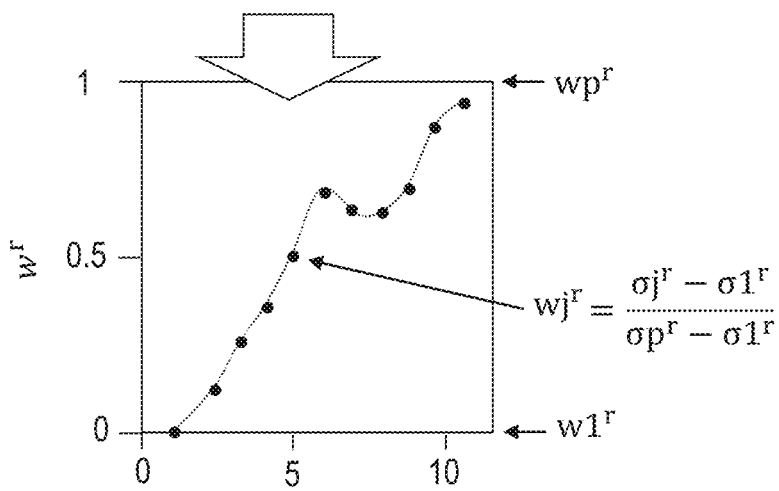

The invention also provides for the capability to modify the k components thus selected in step 130 (symbolized by the vector $\phi'$ in FIG. 7), prior to the implementation of step 140, whether said components were produced in step 120 by a principal component analysis or by an alternative technique (spherical harmonics, Fourier transform, etc.). In the case of an implementation of a principal component analysis, the q components produced are known hereinafter as "principal components". The objective is to increase the contributions of the most "informative" principal components (the ranks of which are the lowest) with respect to those the respective capacities of which to express items of spatial information are lower, those of higher ranks. To this end, such a step 130 can also include a sub-step 133 of applying an operation of filtering the k principal components selected, the filtering intensity of which is specific to each of the k principal components of ranks 1 to k (less than or equal to q) selected and proportional to the informative indicator $\bar{\sigma}1^r$ to $\bar{\sigma}k^r$ thereof. Such a filtering operation 133 can consist of the use, alone or in combination, of a Gaussian filter, a mean filter, a median filter, an anisotropic diffusion filter, a wavelet filter, or any filter, spatial or other, capable of being used in this context. By way of preferred but non-limitative example, such a sub-step 133 can consist of the adjustment of weights $wj^r$ specific to the principal components of ranks j carried out on the basis of the values $\bar{\sigma}j^r$. In this example, the weights can be multiplied linearly by the power A of a Gaussian filter. Each component selected, i.e. of rank j, j being less than or equal to k, is filtered by a factor of $wj^r \times A$. In a variant, or in addition to the linear multiplication, the weights can be expressed beforehand in the form of inputs of a logarithmic, exponential or polynomial function f. In this way, each selected score image of PCj, i.e. of rank j, j being less than or equal to k, can be filtered by a factor defined by $f(wj^r) \times A$. Finally, the "filtered" score images are used to reproduce the matrix of scores U. As shown in FIG. 15, such a weight $wj^r$ can be calculated on the basis of the curve "$\bar{\sigma}j^r$" or shown in FIG. 9, as follows:

$$wj^r = \frac{\bar{\sigma}j^r - \bar{\sigma}1^r}{\bar{\sigma}p^r - \bar{\sigma}1^r}$$

where $\bar{\sigma}j^r$ is the value of the informative indicator of the principal component of rank j, $\bar{\sigma}1^r$ is the value of the informative indicator of the principal component of rank 1 and $\bar{\sigma}p^r$ the value of the plateau of the curve "$\bar{\sigma}j^r$" described by said informative indicators $\Sigma^r$. Thus, such a weight $wj^r$ is comprised between $w1^r=0$ and $wp^r=1$ (i.e. when the curve "$\bar{\sigma}j^r$" has reached a plateau $\bar{\sigma}p^r$).

The invention is not to be considered limited to only these examples of calculations of the weights $wj^r$ of the sub-step 133.

Figure 10:
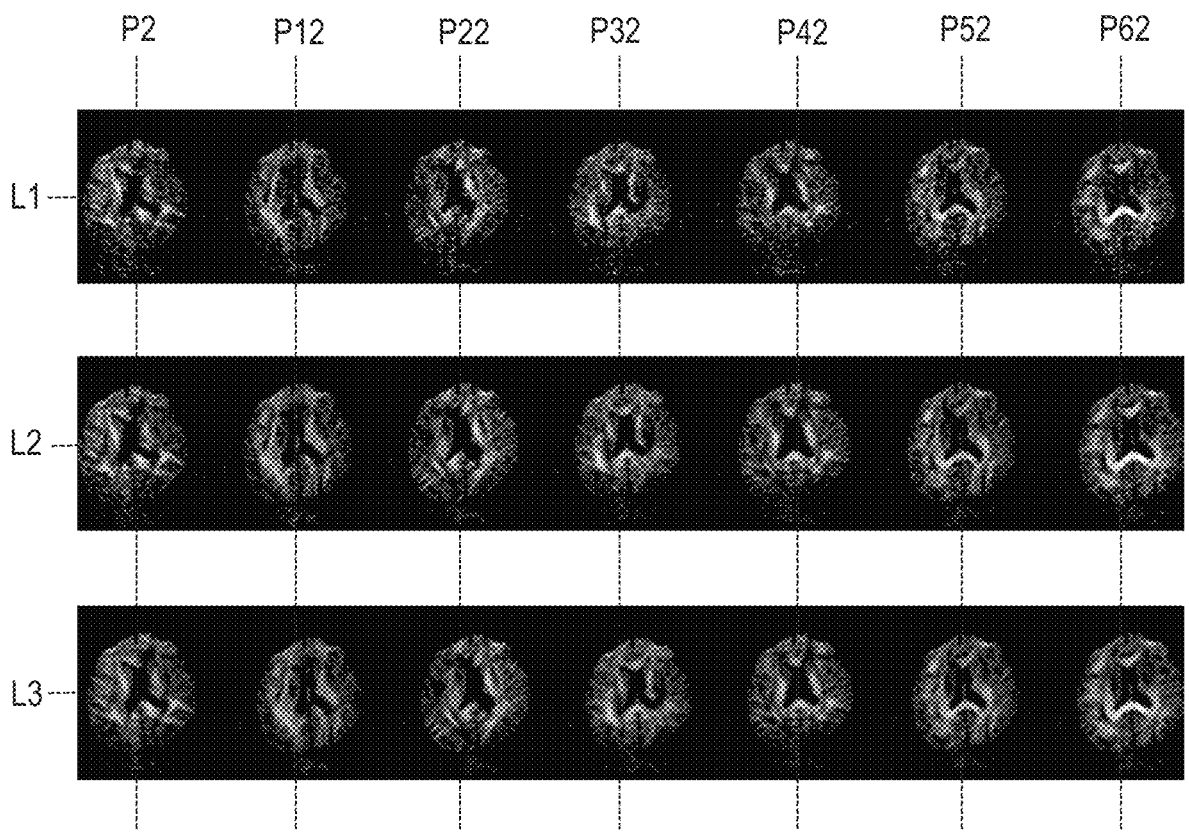
FIG. 10 shows an example attenuation of the noise in HARDI diffusion experimental data for different phases.
Figure 11:
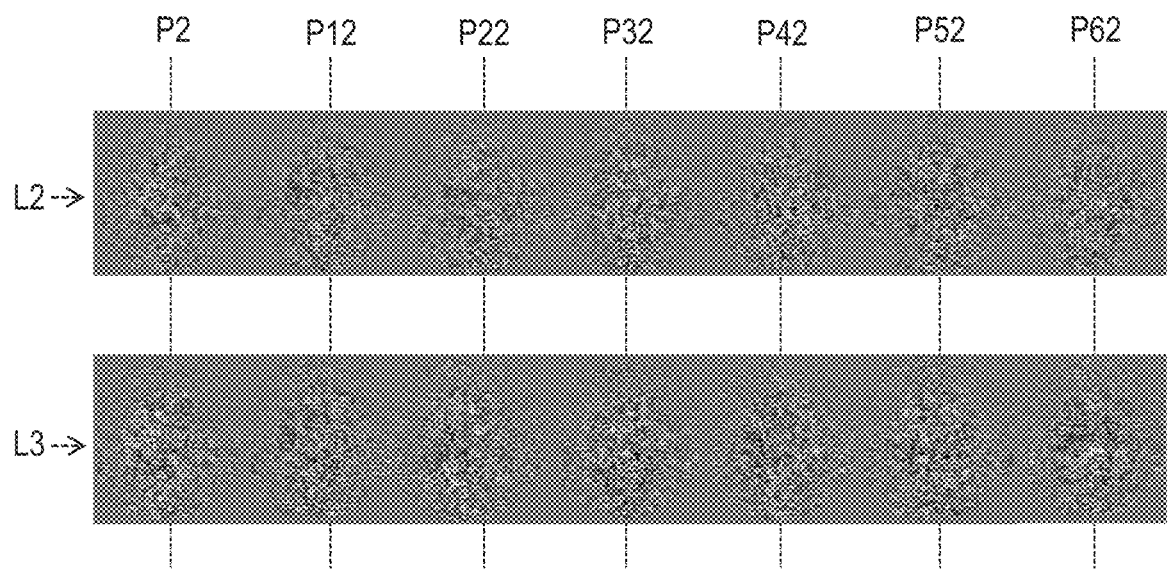
FIG. 11 shows an example of noise removed by implementation of the invention from such HARDI data for different phases.
Figure 12:
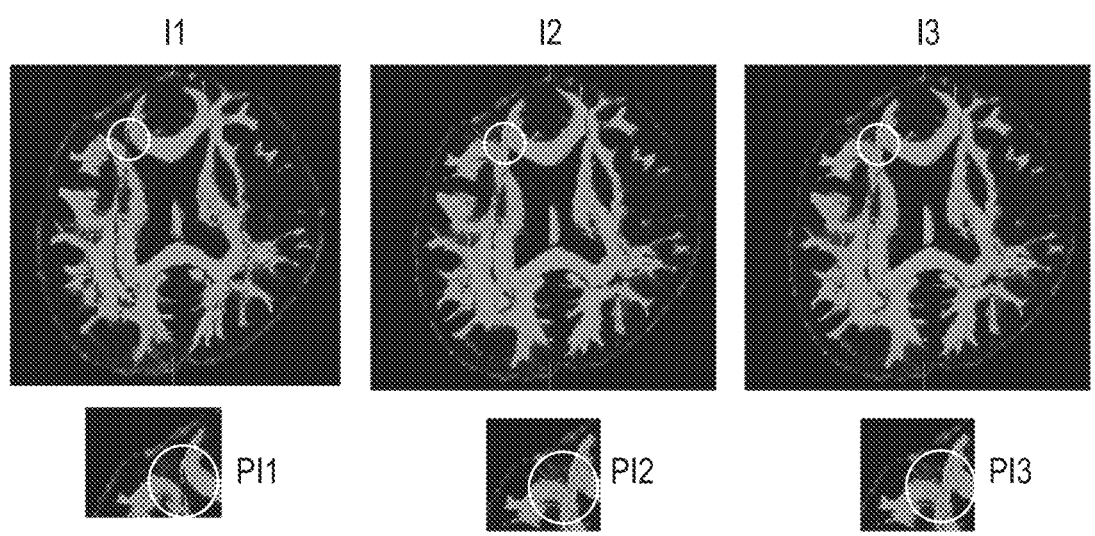
FIG. 12 shows an example of use and the benefit resulting from such a use of data denoised by virtue of the invention in the field of tractography.

FIGS. 10 to 12 make it possible to show the benefit resulting from the implementation of a method for attenuating the noise in experimental data originating from multiple acquisitions by a magnetic resonance imaging device in the HARDI diffusion imaging field. Such an acquisition of experimental data can thus bear on a plurality of slices, in this case a human brain, for a plurality of phases. FIG. 10 thus shows the raw data, for a given slice, of phases two, twelve, twenty-two, thirty-two, forty-two, fifty-two and sixty-two, respectively referenced P2, P12, P22, P32, P42, P52 and P62 in FIG. 10. The first series of images referenced L1 show the raw, therefore noisy, experimental data for a plurality of voxels and respectively for the different phases P2 to P62 mentioned above. The second and third series of images L2 and L3 show said experimental data denoised by the implementation of the invention, according to which the k principal components selected were subjected to a filtering (step 133 of a method according to FIG. 7) prior to (L3) or not prior to (L2) the projection of the experimental data onto said k principal components. The increasing enhancement contributed by the invention can be noted visually from series L1 to series L3.

In addition, the performances of a method 100 according to the invention can be shown in FIG. 11, which depicts the noise removed in step 140 of a method according to the invention, for the different phases referenced P2, P12, P22, P32, P42, P52 and P62 in FIG. 10, pertaining to the denoised experimental data of series L2 and L3 in FIG. 10. It is clear that such noise does not reveal any spatial information of interest.

FIG. 12 depicts the use of HARDI diffusion data described with reference to FIG. 10 in the context of tractography. FIG. 12 shows three colour images 11, 12, 13, expressed in grayscale, for a given slice, as well as a partial enlargement P11, P12 and PI3 of each image I1, I2, I3. These latter were produced in a step 150 on the basis of respectively raw experimental data (series L1 in FIG. 10), data denoised by implementation of the invention and as shown by the series L2 in FIG. 10, and by the series L3 in said FIG. 10. Said enlargements PI1, P12 and PI3 make it possible to see with the naked eye an increasing highlighting of fibres. In the enlargement PI1, an area (circled in white) of the organ could be considered to be dead, which is not the case in the enlargements P12 and PI3. Moreover, such a use makes it possible to count such fibres. On the basis of the raw data of series L1 in FIG. 10, it is possible to count of the order of twenty-seven thousand fibres. These are of the order of thirty-four thousand if denoised data forming the series L2 in FIG. 10 are used, and over thirty-seven thousand if the denoised data forming the series L3 in FIG. 10 are used. A denoising of experimental data according to the invention thus contributes a particularly significant enhancement.

Figure 13:
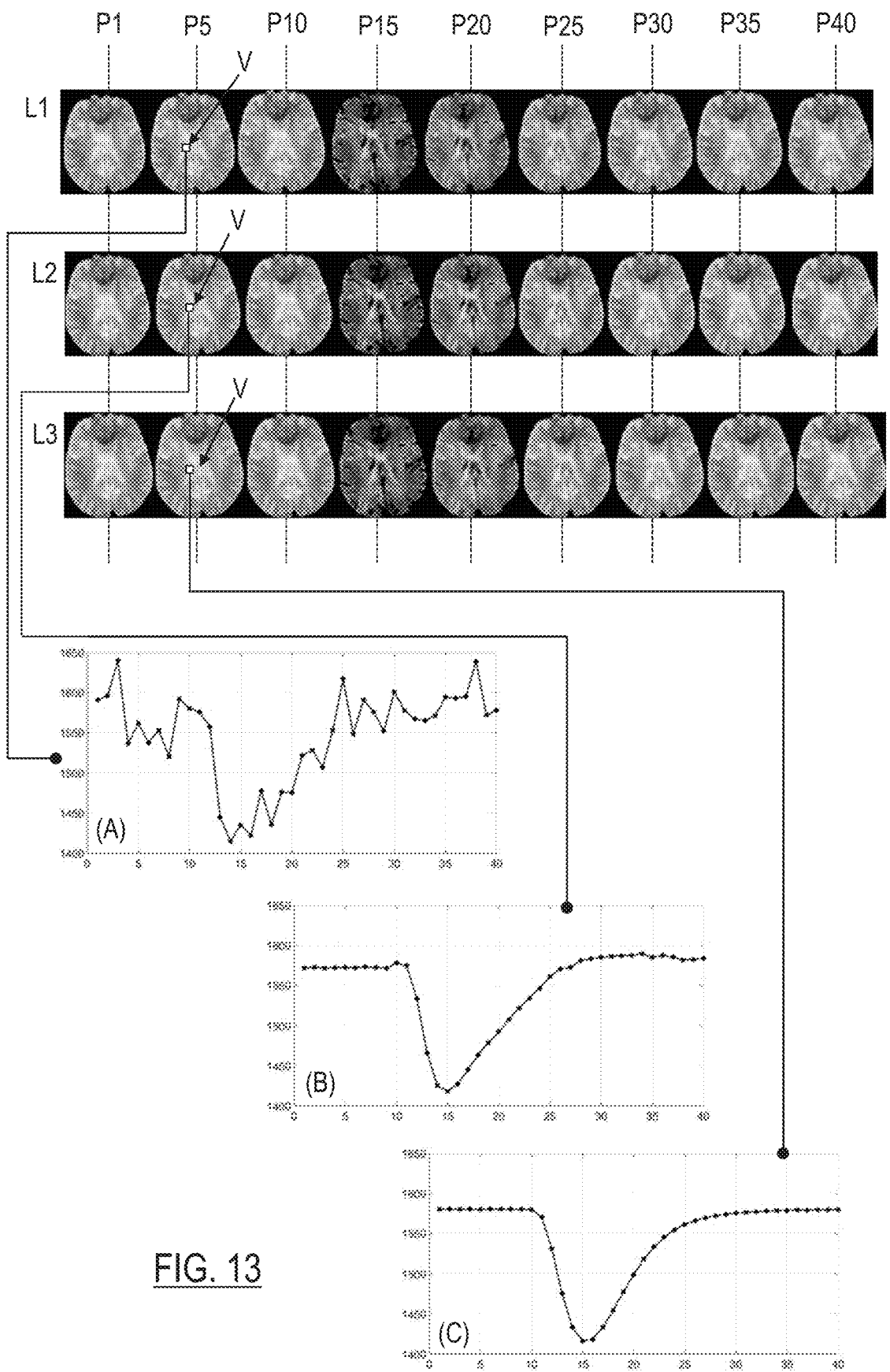
FIG. 13 shows an example attenuation of the noise in experimental perfusion data for different phases.
Figure 14:
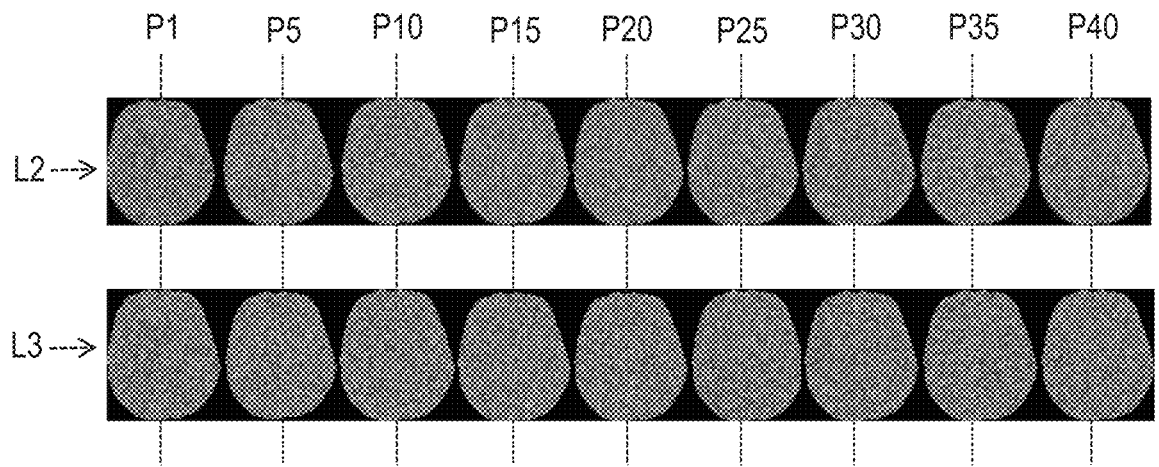
FIG. 14 shows an example of noise removed by implementation of the invention from such perfusion data for different phases.

FIGS. 13 and 14, like FIGS. 10 and 11, show the enhancement contributed by the invention on the basis of perfusion data. Thus, the acquisition of experimental data bears on a plurality of slices, in this case a human brain, for a plurality of phases. FIG. 13 thus shows the raw data, for a given slice, of phases one, five, ten, fifteen, twenty, twenty-five, thirty, thirty-five and forty, respectively referenced P1, P5, P10, P15, P20, P25, P30, P35 and P40 in FIG. 13. The first series of images referenced L1 show the raw, therefore noisy, experimental data for a plurality of voxels and respectively for the different phases P1 to P40 mentioned above. The second and third series of images L2 and L3 show said experimental data denoised by the implementation of the invention, according to which the k principal components selected were subjected to a filtering (step 133 of a method according to FIG. 7) prior to (L3) or not prior to (L2) the projection of the experimental data onto said k principal components. The increasing enhancement contributed by the invention can be noted visually from series L1 to series L3. This enhancement is even more noteworthy when, in said FIG. 13, the spectrum of the experimental data is examined, for a voxel V of interest, respectively raw (A), denoised by the implementation of the invention when the k principal components selected were not subjected to a filtering (B) and when said filtering has been carried out (C). It is notable that the curves respectively described by said spectra are increasingly smooth.

In addition, the performances of a method 100 according to the invention can be shown in FIG. 14, which depicts the noise removed pertaining to the series L2 and L3 in FIG. 13. It is clear that such a noise does not reveal any spatial information of interest.

In the foregoing description, the concepts that underlie the invention have been described through an exemplary implementation applied to data obtained by magnetic resonance imaging. It will be appreciated, however, that these concepts can be equally applied to other types of medical imaging, such as CT scans and sonograms. Moreover, they are not limited to medical imaging data. They could be utilized in other fields of application from the point at which noisy images or volumes of noisy images are acquired repetitively or sequentially, such as for example the cinema, identity control, etc.

The invention claimed is:

1. A system for attenuating the noise in experimental data originating from multiple acquisitions by a nuclear magnetic resonance imaging device pertaining to an elementary volume of interest, hereinafter named "voxel" of interest, among a plurality of voxels, said system comprising a processor configured to implement the following operations:
   acquiring said experimental data pertaining to the plurality of voxels;
   projecting the experimental data into a base of functions or vectors to produce a set of q components as well as their respective scores for the plurality of voxels, said scores corresponding to the projection of said experimental data onto said q components;
   selecting k components among the q components produced,
   wherein the selection of the k components includes:
      producing score images of the components for the plurality of voxels and informative indicators quantifying the spatial information contained in said images of the scores associated with said components in the form of a rate of decrease of the values of a determined characteristic of said scores before and after application of a smoothing filter to said scores, said determined characteristic of the scores for a plurality of voxels belonging to a set of characteristics, alone or in combination, including variance, standard deviation, median and mean, and
      determining the k components on the basis of said informative indicators;
   projecting said experimental data onto the selected k components and producing noise-attenuated experimental data pertaining to the elementary volume; and
   generating a human-perceptible representation of a physiological signal based upon the noise-attenuated experimental data.

2. The system of claim 1, wherein:
   the production of q components as well as their respective scores for the plurality of voxels produces an ordered set of q components according to a determined order relation; and
   the determination of the k components comprises determining the rank k in order to select the first k components on the basis of said informative indicators.

3. The system of claim 2, where the production of q components as well as their respective scores for the plurality of voxels comprises implementing a principal component analysis to produce an ordered set of q principal components according to their respective eigenvalues.

4. The system of claim 2, wherein the determination of the rank k comprises calculating the mathematical difference between values of said informative indicators which are ordered in accordance with the q components, the rank k being that of the component for which said mathematical difference falls below, or becomes equal to, a determined threshold.

5. The system of claim 2, wherein the determination of the rank k comprises detecting a plateau described by the values of the informative indicators which are ordered according to the q components, from the informative indicator of the component of rank q to the informative indicator of the component of rank 1, the rank k being that of the first component the value of the informative indicator which deviates from said plateau.

6. The system of claim 2, wherein the determination of the k components comprises detecting a plateau described by the values of the informative indicators which are ordered according to an order relation, the k components selected being those for which their respective informative indicators deviate from said plateau.

7. The system according to claim 1, wherein:
   the experimental data pertaining to the plurality of voxels result from a multiphase diffusion imaging acquisition by the magnetic resonance imaging device; and the production of q components as well as their respective scores for the plurality of voxels comprises implementing a spherical harmonic decomposition.

8. The system according to claim 1, wherein:
the experimental data pertaining to the plurality of voxels result from a multiphase acquisition by a functional magnetic resonance imaging device; and
the production of q components as well as their respective scores for the plurality of voxels comprises implementing a Fourier transform decomposition.

9. The system of claim 1, wherein the determination of the k components comprises calculating the mathematical difference between successive values of said informative indicators which are ordered according to a determined order relation, the k components selected being those for which said mathematical difference between the values of their informative indicators remains above a determined threshold.

10. The system of claim 1, wherein the processor is further configured to apply a filtering operation of the selected k components, the filtering intensity of which is specific to each of the selected k components and proportional to the informative indicator thereof.

11. The system according to claim 10, wherein the filtering operation comprises the use, alone or in combination, of a Gaussian filter, a mean filter, a median filter, an anisotropic diffusion filter.

12. A non-transitory computer-readable storage medium including one or more program instructions that can be interpreted by the processor of said system, said program instructions being capable of being loaded in non-volatile storage of said system, wherein the execution of said instructions by said processor causes the implementation of the operations set forth in claim 1.

13. A method for attenuating the noise in experimental data originating from multiple acquisitions by a nuclear magnetic resonance imaging device pertaining to an elementary volume of interest, hereinafter named "voxel" of interest, comprising:
acquiring said experimental data pertaining to the plurality of voxels;
projecting the experimental data into a base of functions or vectors to produce a set of q components as well as their respective scores for the plurality of voxels, said scores corresponding to the projection of said experimental data onto said q components;
selecting k components among the q components produced,
wherein the selection of the k components includes:
producing score images of the components for the plurality of voxels and informative indicators quantifying the spatial information contained in said images of the scores associated with said components in the form of a rate of decrease of the values of a determined characteristic of said scores before and after application of a smoothing filter to said scores, said determined characteristic of the scores for a plurality of voxels belonging to a set of characteristics, alone or in combination, including variance, standard deviation, median and mean, and
determining the k components on the basis of said informative indicators;
projecting said experimental data onto the selected k components and producing noise-attenuated experimental data pertaining to the elementary volume; and
generating a human-perceptible representation of a physiological signal based upon the noise-attenuated experimental data.

14. A system for attenuating the noise in experimental data originating from multiple acquisitions by a medical imaging device pertaining to an elementary volume of interest, hereinafter named "voxel" of interest, among a plurality of voxels, said system comprising a processor configured to implement the following operations:
acquiring said experimental data pertaining to the plurality of voxels;
projecting the experimental data into a base of functions or vectors to produce a set of q components as well as their respective scores for the plurality of voxels, said scores corresponding to the projection of said experimental data onto said q components;
selecting k components among the q components produced,
wherein the selection of the k components includes:
producing score images of the components for the plurality of voxels and informative indicators quantifying the spatial information contained in said images of the scores associated with said components in the form of a rate of decrease of the values of a determined characteristic of said scores before and after application of a smoothing filter to said scores, said determined characteristic of the scores for a plurality of voxels belonging to a set of characteristics, alone or in combination, including variance, standard deviation, median and mean, and
determining the k components on the basis of said informative indicators;
projecting said experimental data onto the selected k components and producing noise-attenuated experimental data pertaining to the elementary volume; and
generating a human-perceptible representation of a physiological signal based upon the noise-attenuated experimental data.

15. A method for attenuating the noise in experimental data originating from multiple acquisitions by a medical imaging device pertaining to an elementary volume of interest, hereinafter named "voxel" of interest, comprising:
acquiring said experimental data pertaining to the plurality of voxels;
projecting the experimental data into a base of functions or vectors to produce a set of q components as well as their respective scores for the plurality of voxels, said scores corresponding to the projection of said experimental data onto said q components;
selecting k components among the q components produced,
wherein the selection of the k components includes:
producing score images of the components for the plurality of voxels and informative indicators quantifying the spatial information contained in said images of the scores associated with said components in the form of a rate of decrease of the values of a determined characteristic of said scores before and after application of a smoothing filter to said scores, said determined characteristic of the scores for a plurality of voxels belonging to a set of characteristics, alone or in combination, including variance, standard deviation, median and mean, and
determining the k components on the basis of said informative indicators;

projecting said experimental data onto the selected k components and producing noise-attenuated experimental data pertaining to the elementary volume; and
generating a human-perceptible representation of a physiological signal based upon the noise-attenuated experimental data.

\* \* \* \* \*